United States Patent
Farrell et al.

[19]
[11] Patent Number: 6,053,313
[45] Date of Patent: Apr. 25, 2000

[54] CATHETER PACKAGING SYSTEM

[75] Inventors: Thomas Farrell; Kevin Treacy, both of Galway, Ireland; William A. Berthiaume, Hudson; Randall W. Davis, Chelmsford, both of Mass.

[73] Assignee: AVE Connaught, Galway, Ireland

[21] Appl. No.: 09/091,923

[22] PCT Filed: Oct. 22, 1997

[86] PCT No.: PCT/IE97/00070

§ 371 Date: Jun. 24, 1998

§ 102(e) Date: Jun. 24, 1998

[87] PCT Pub. No.: WO98/18515

PCT Pub. Date: May 7, 1998

[30] Foreign Application Priority Data

Oct. 25, 1996 [IE] Ireland ..................................... 960752

[51] Int. Cl.$^7$ ......................... B65D 85/671; A61M 29/00
[52] U.S. Cl. ........................... 206/364; 206/438; 606/192
[58] Field of Search ..................... 206/364, 438; 606/192

[56] References Cited

U.S. PATENT DOCUMENTS

| | | |
|---|---|---|
| 3,203,545 | 8/1965 | Grossman . |
| 3,794,042 | 2/1974 | De Klotz et al. .................... 206/364 X |
| 4,262,800 | 4/1981 | Nethercutt ................................ 206/364 |
| 4,823,167 | 4/1989 | Manska et al. ...................... 206/364 X |
| 5,031,775 | 7/1991 | Kane ..................................... 206/364 X |
| 5,217,114 | 6/1993 | Gadberry et al. . |
| 5,344,011 | 9/1994 | DiBernardo et al. . |
| 5,591,194 | 1/1997 | Berthiaume ............................. 606/192 |
| 5,658,309 | 8/1997 | Berthiaume et al. ................... 606/192 |
| 5,846,259 | 12/1998 | Berthiaume ............................. 606/192 |

FOREIGN PATENT DOCUMENTS

WO 9602290  2/1996  WIPO .

Primary Examiner—Bryon P. Gehman
Attorney, Agent, or Firm—Sterne, Kessler, Goldstein & Fox PLLC

[57] ABSTRACT

A package is provided for a catheter which comprises an elongate tube, having a proximal end and a distal end, for receiving a catheter shaft. The proximal end includes a sleeve element sized to accommodate one or more catheter shaft accessories located on the proximal end of the catheter, and a retainer portion for releasably retaining the catheter and catheter shaft accessories. The retainer portion is engageable with the sleeve element and is axially slidable relative thereto, between a storage state in which the retainer portion and the retained catheter shaft accessories are located substantially within the sleeve element and a usable state in which the retainer portion and the retained catheter shaft accessories are withdrawn from the sleeve element.

13 Claims, 11 Drawing Sheets

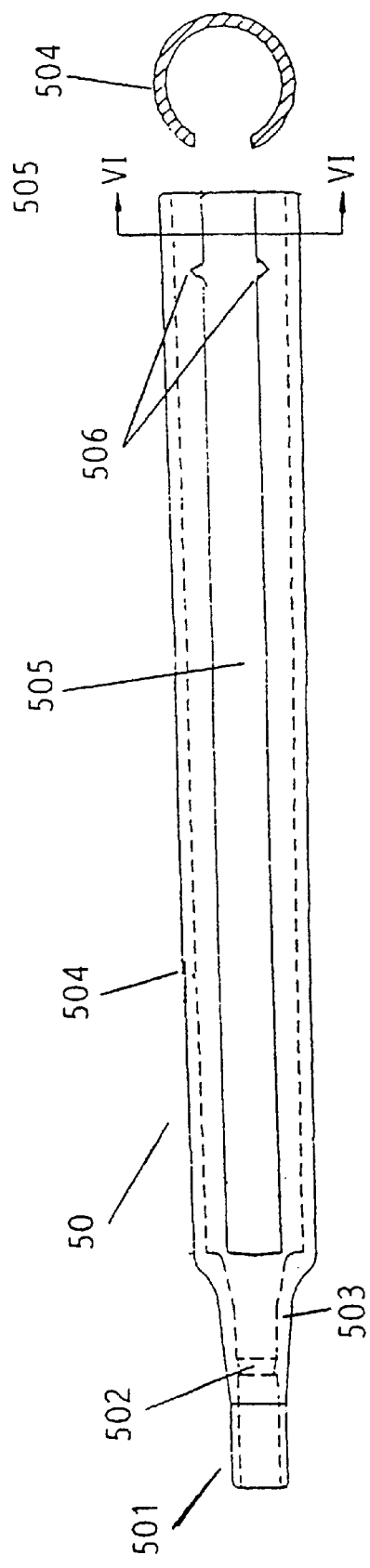
FIGURE 5
FIGURE 6
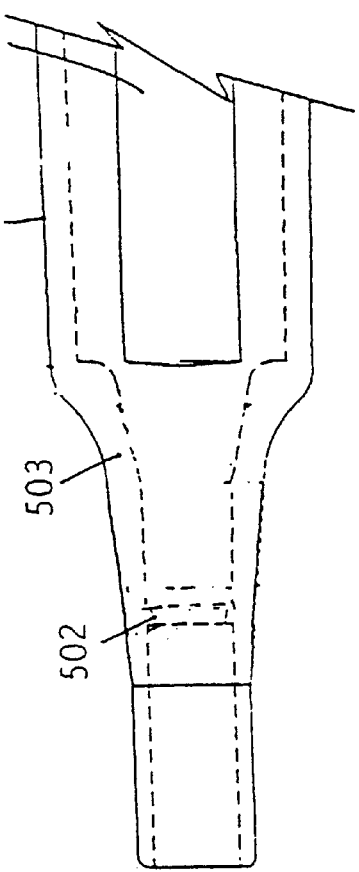
FIGURE 7

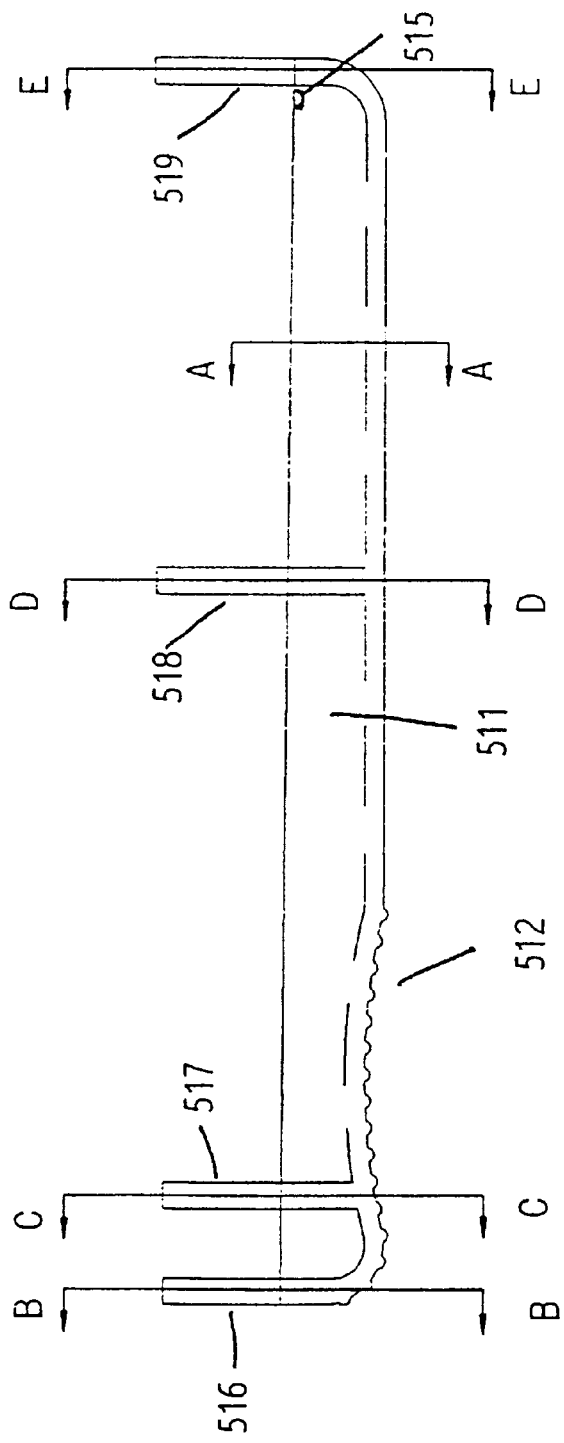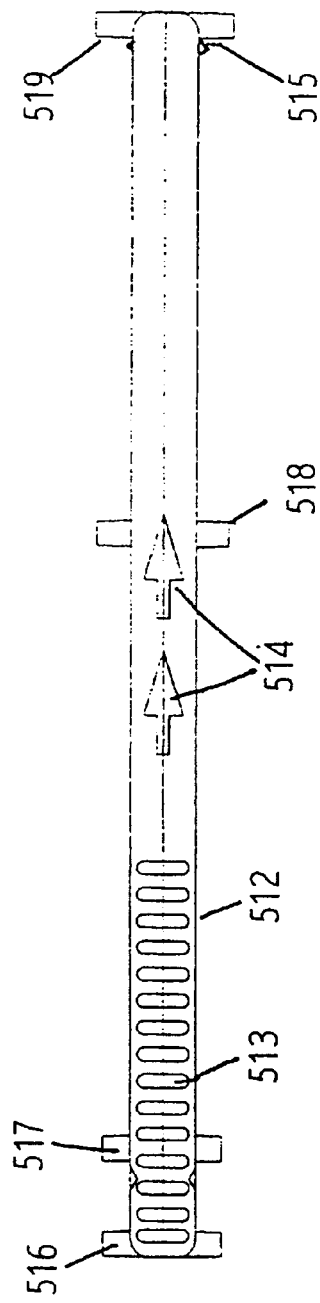
FIGURE 9
FIGURE 10

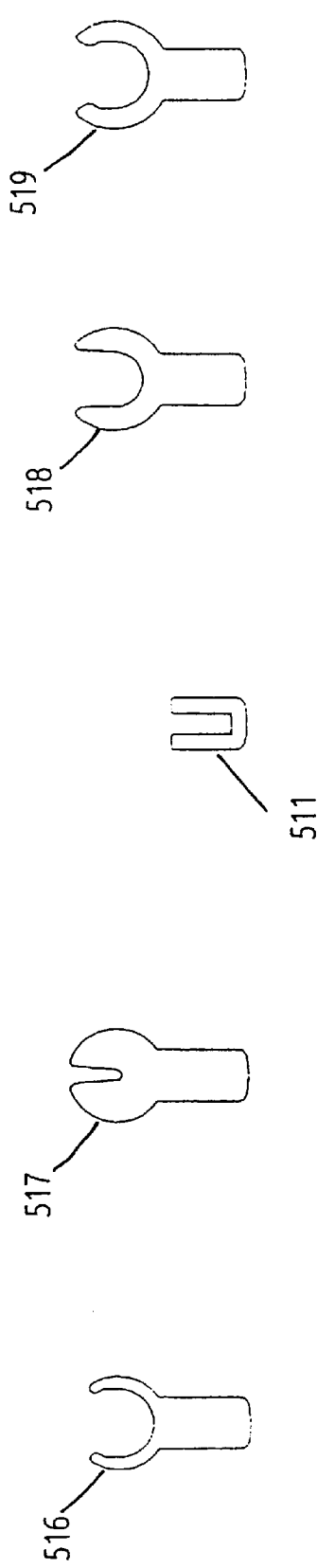

CATHETER PACKAGING SYSTEM

BACKGROUND OF THE INVENTION

1. Field of the Invention

The present invention relates to an improved catheter packaging system for use particularly, but not exclusively with a percutaneous translumenal coronary angioplasty (PTCA) catheter.

2. Description of the Related Art

Catheters typically have fittings or accessories of some kind on their proximal end, that is to say, the end of the catheter which, in use, is not contained within the patient's body. PTCA or balloon catheters generally have a luer fitting at the proximal end and will usually have one or more shaft accessories, such as a wire lock device and an anti-backbleed device. The bulk of the length of the catheter is typically packaged within a robust dispenser tube, which protects the balloon located on the distal end of the shaft and the shaft itself from accidental damage during storage, transit and preparations for use. Normally, the dispenser tube is coiled to enable the product to be packaged more compactly. The proximal end of the catheter comprising the luer fitting and shaft accessories projects clear of the tube so that it is presented free for use by the physician. The distal end of the catheter, which includes the delicate balloon, is retained safely within the coiled dispenser. While the distal end is securely protected during transit and storage, the proximal end is subject to damage in these phases. It will be appreciated that any movement of the package which tends to move the exposed proximal end relative to the dispenser is likely to cause kinking of the catheter which renders it useless. Furthermore, incorrect removal of the catheter from its package can cause kinking of the catheter. For example, if there is a lateral component to the substantially axially applied force (relative to the longitudinal axis of the dispenser) used to withdraw the catheter from the dispenser, this can induce a kink in the catheter. Likewise, exertion of a rotational force can cause the catheter to rotate within the coiled dispenser, but since such rotational freedom is resisted by the coiling of the dispenser, damage to the catheter shaft can result.

Packages for catheters are known in which the proximal end and its accessories are presented to the physician in the correct orientation for removal. In one such packaging device, a thermoformed plastics clip is provided which is shaped to receive and retain the luer fitting and accessories as a snap-fit. The clip is also shaped to retain the proximal end of the coiled dispenser so that prior to use, the dispenser, catheter and proximal end accessories are fixed together, the presentation being the one required for correct removal of the catheter from the dispenser. This can be achieved by removing the luer fitting and accessories from the thermoformed clip, then withdrawing the catheter. In practice, it has been found that in the busy environment of the hospital, there is a tendency for the luer to be pulled out of the clip in a motion which is at an angle to the longitudinal shaft of the catheter and, as described above, this can result in damage to the shaft. Additionally, it has been found that since the clip is relatively weak, it is susceptible to breakage during transit and storage and this can result in shaft damage.

In another known package, a sleeve is formed on or fixed to the proximal end of the dispenser and sized to receive and retain the accessories and a portion of the luer fitting. The luer fitting projects from the sleeve so that it can be grasped to withdraw the catheter from the dispenser. While this arrangement is quite successful, it is frequently the case that when the luer is withdrawn, one or more of the accessories remains within the sleeve.

SUMMARY OF THE INVENTION

The present invention seeks to overcome the disadvantages of the currently available PTCA packages by providing a package which is easy to use and which reliably presents the proximal end of a catheter and its accessories, in correct orientation for removal from the package.

The present invention provides a package for a catheter comprising an elongate tube for receiving a catheter shaft, each of the tube and the catheter shaft having a proximal end and a distal end, the proximal end of the tube including a sleeve element sized to accommodate at least one catheter shaft accessory located on the proximal end of the catheter and a retaining member for releasably retaining the catheter shaft and any catheter shaft accessory, the retaining member being engageable with the sleeve element and being axially slidable relative to the sleeve element between a storage state in which the retaining member, catheter shaft and any retained catheter shaft accessory are located substantially within the sleeve element and a usable state in which it and the catheter are withdrawn from the sleeve element.

Preferably, guide means are provided to guide the retaining member to be removable from the sleeve element along an axis which is co-axial with the longitudinal axes of the sleeve element and the tube. The guide means may comprise a slot, groove or track formed along the longitudinal axis of the sleeve element and the retaining member may comprise a key which is engageable with the slot, groove or track of the sleeve element.

In a preferred arrangement the guide means comprises a slot and the retaining member includes a key sized substantially to match the length and width dimensions of the slot. A portion of the key preferably extends axially outwardly of the slot and that portion is conveniently shaped to be gripped by a user to facilitate removal of the retainer member from the sleeve element.

The axially outwardly extending portion of the key may include a ridged depression sized to receive a user's finger-pad to assist the user in sliding the retaining means relative to the sleeve element.

Conveniently, the retaining member may further comprise at least one gripping means for releasably retaining a catheter shaft and/or catheter shaft accessory or accessories. The gripping means may comprise a deformable flexible member sized and arranged to receive the catheter shaft or accessory as a snap fit.

Flushing means are conveniently provided at the distal end of the tube for enabling the interiors of the tube and the catheter contained within the tube to be flushed with flushing fluid from their respective distal to proximal ends.

Preferably, the sleeve element includes a neck portion which is sized and shaped to form a seal between the interior of the proximal end of the tube and the exterior of the proximal end of the catheter shaft, so that flushing fluid is prevented from emerging from the proximal end of the tube thereby ensuring that flushing fluid which issues in the region of the proximal ends has flowed through the interior of the catheter shaft. A viewing port may be formed in the sleeve adjacent the terminus of the proximal end of the catheter shaft for enabling the user to view the flushing fluid emerging from the terminus. Conveniently, the sleeve element is formed integrally with the tube.

BRIEF DESCRIPTION OF THE DRAWINGS

The invention will now be described more particularly with reference to the accompanying drawings in which:

FIG. 5 is a plan view of the sleeve portion of the link device of the invention;

FIG. 6 is a sectional view along line VI—VI of FIG. 5;

FIG. 7 is an enlarged view of the neck end of the sleeve portion of FIG. 5;

FIG. 9 is a side view of the retainer portion of the link device;

FIG. 10 is a plan view from below of the retainer;

FIGS. 11 to 15 are sectional views along the lines A—A, B—B, C—C, D—D and E—E respectively of FIG. 9;

DETAILED DESCRIPTION OF THE INVENTION

Figure 1:
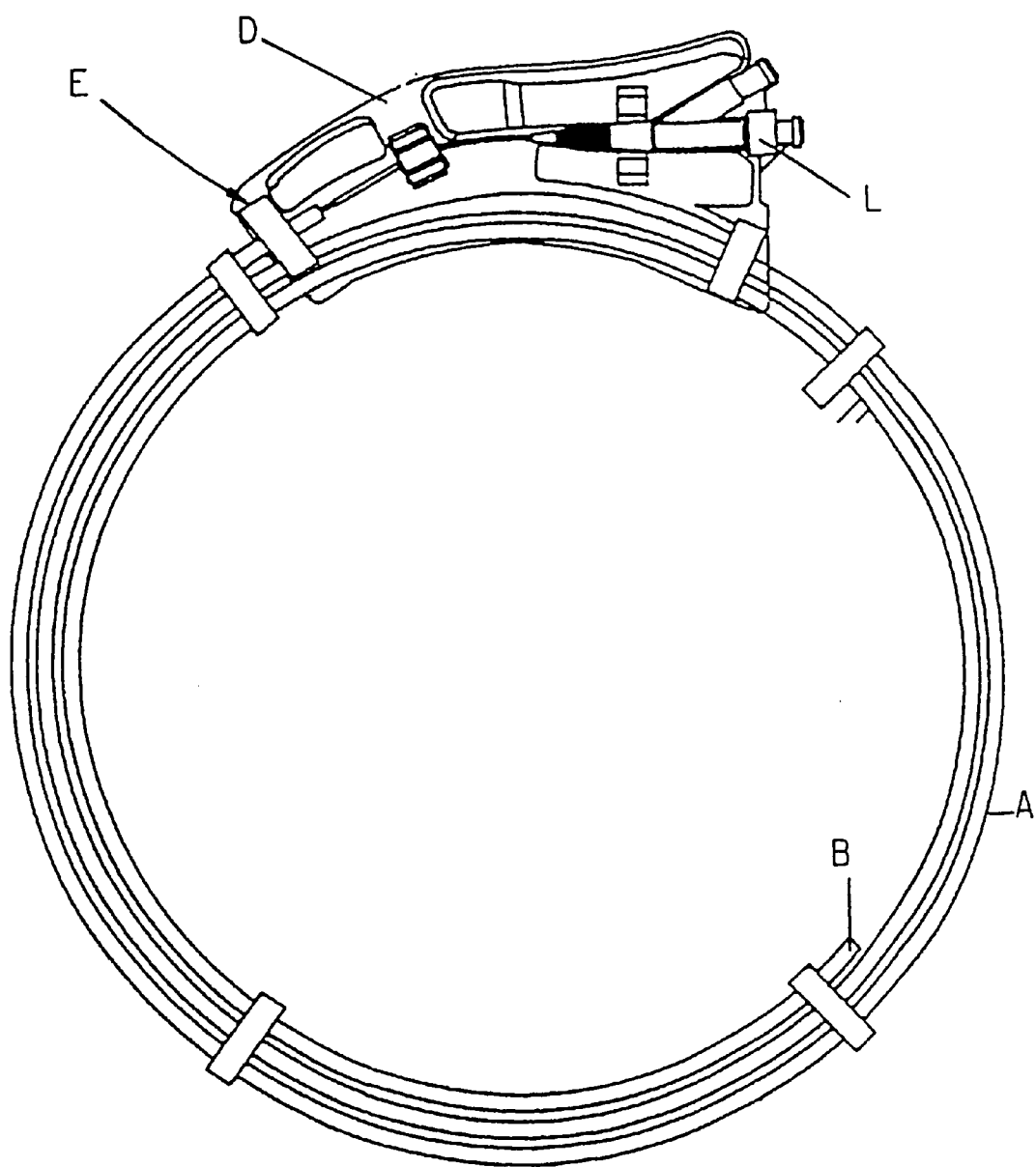
FIG. 1 is a plan view of a prior-art package for an over-the-wire type PTCA catheter.

Referring firstly to FIG. 1, a prior art PTCA catheter package comprises a coiled dispenser A along the length of which the flexible catheter shaft (not shown) is retained, the distal (balloon) end of the shaft being located during storage in the region of the distal end B of the dispenser A. The proximal end of the shaft, including the luer fitting L and other shaft accessories, is retained by snap-fit in a thermoformed clip D, shaped to receive the various parts of the proximal end. A tab E on the thermoformed clip is shaped to snap over the coils of the dispenser, thereby to retain the clip D in correct orientation relative to the dispenser A. The shaft and accessories may be freed from the clip D and depending on the angle of withdrawal, the shaft of the product may be kinked.

Figure 2:
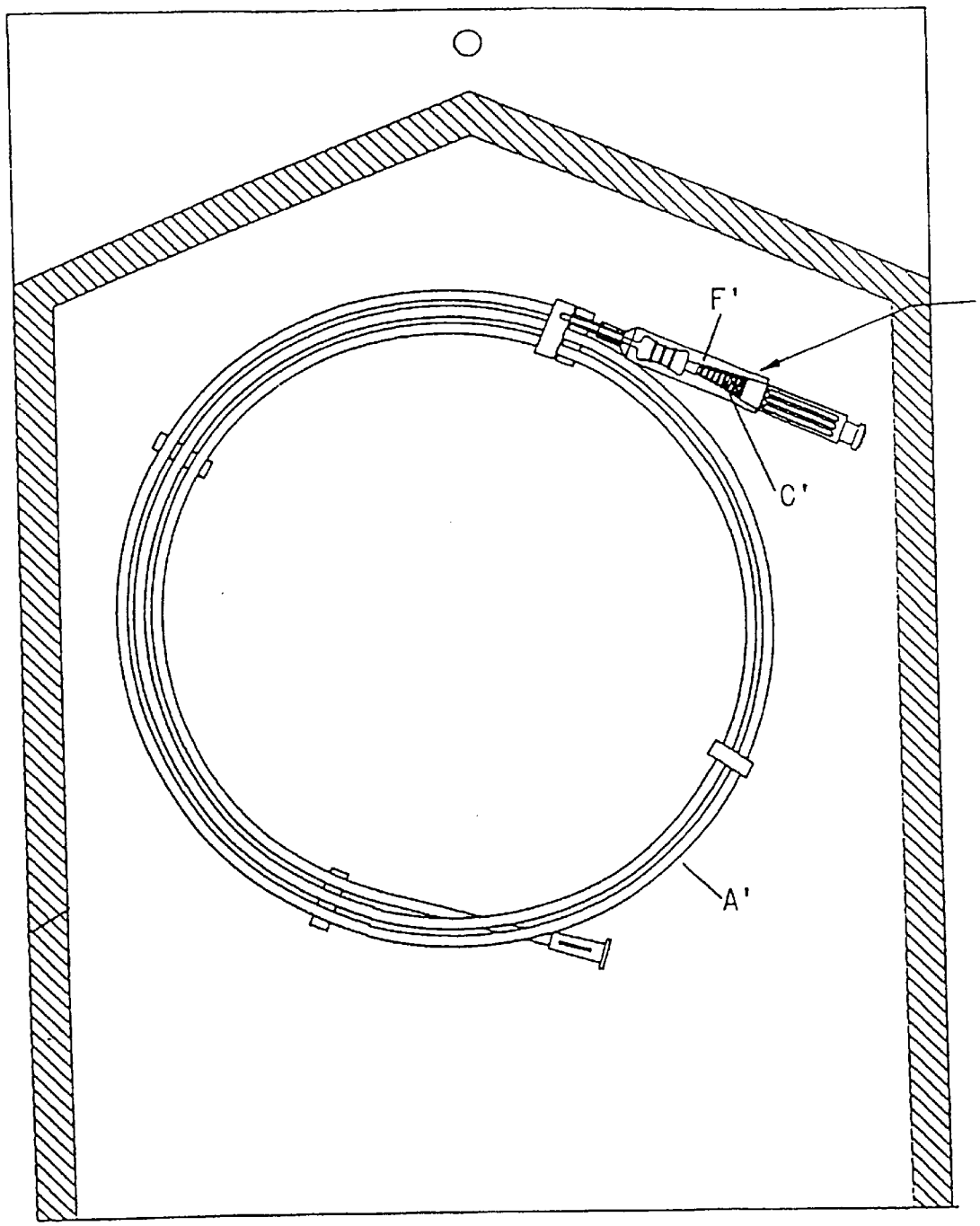
FIG. 2 is a plan view of a prior-art package for a rapid exchange type PTCA catheter.

FIG. 2 illustrates a further prior art package, which as before, includes a coiled dispenser A'. The proximal end of the dispenser includes an injection molded sleeve F', through which extend the proximal end of the shaft, with shaft accessories C'. Thus, the sleeve F' retains the proximal end of the shaft in correct orientation and presentation for removal. To assist in the withdrawal, a portion of the luer fitting extends free of the sleeve. The catheter contained in this type of package is subject to damage by rotational forces exerted upon it on removal from the coiled dispenser.

Figure 3:
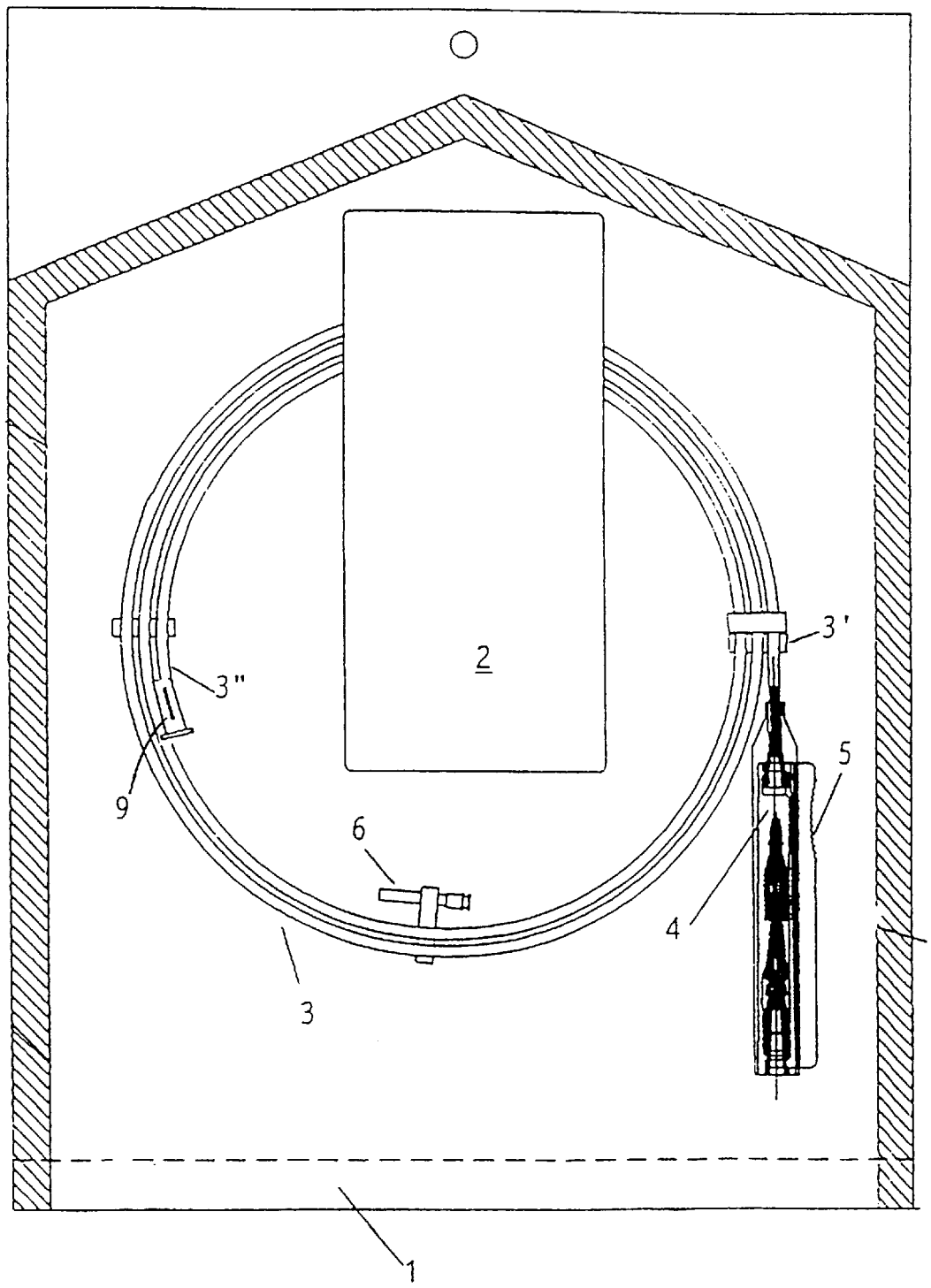
FIG. 3 is a plan view of a PTCA catheter package according to the invention, showing the catheter in the transit/storage position.
Figure 4:
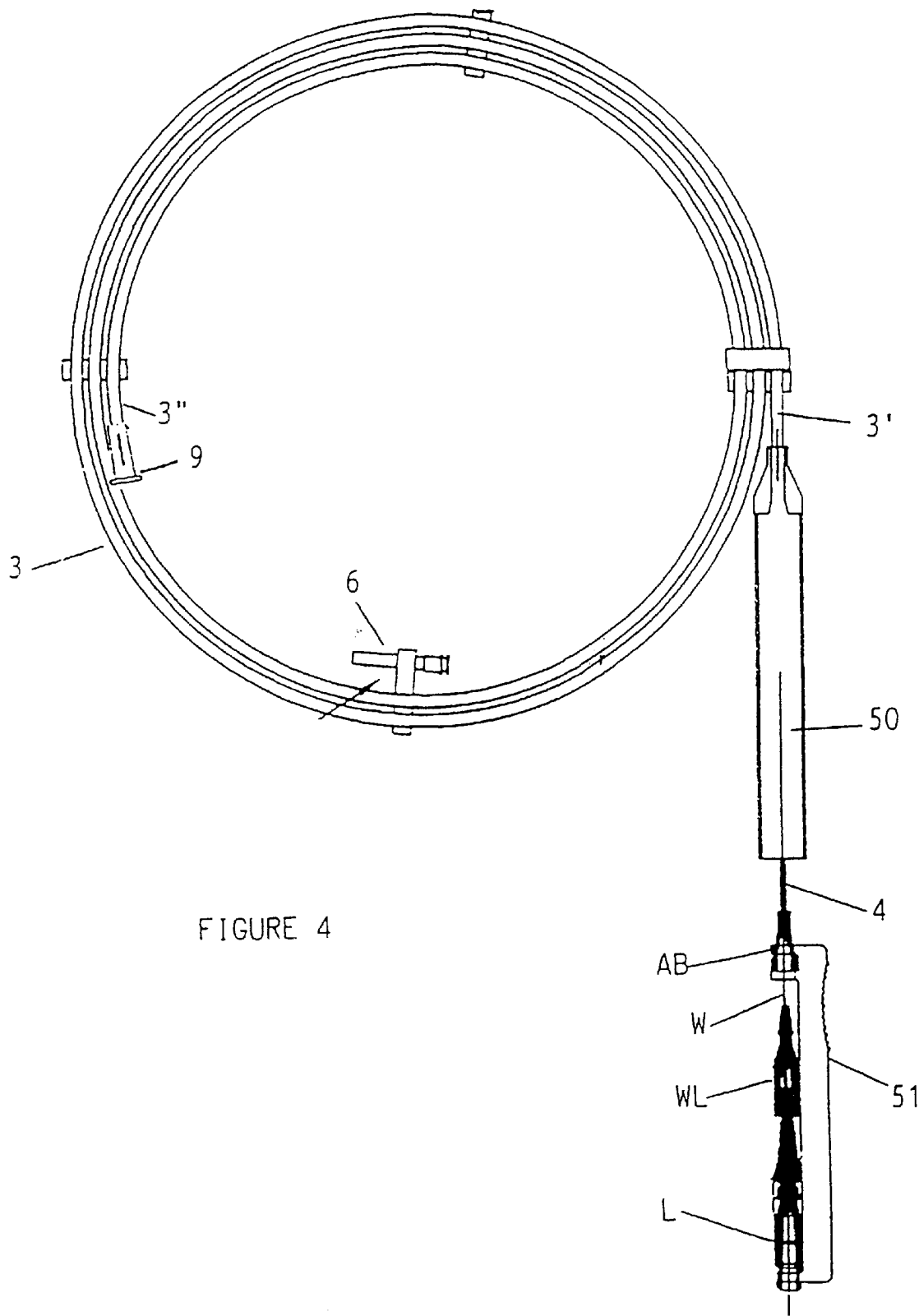
FIG. 4 is a view of the package of FIG. 3 with the pouch removed and the catheter partially withdrawn from the coiled dispenser.

FIG. 3 is a view of the package according to the invention which comprises a chevron pouch 1 overprinted with a product labelling area 2. Within the pouch, the coiled dispenser has a proximal end 3' and a distal end 3" fitted with a tri-lock luer 9 which allows for the direct link up of a syringe with a saline flush solution to flush the catheter in the dispenser. Within the dispenser is contained the flexible catheter shaft 4, the proximal end of which, together with shaft accessories, is retained by link device 5. As can be seen more clearly in FIG. 4, which illustrates the catheter in a partially withdrawn state, the link device 5 includes a sleeve portion 50 connected to the proximal end 3' of the coiled dispenser 3 and a retainer portion 51. The retainer portion 51 positively retains the catheter shaft accessories illustrated, namely an anti-backbleed device AB, a wire-lock device WL and a luer fitting L. The wire W can also be seen in the drawing. The package further includes a flushing tool 6. The use of the tri-lock luer 9 will be described below.

Figure 22:
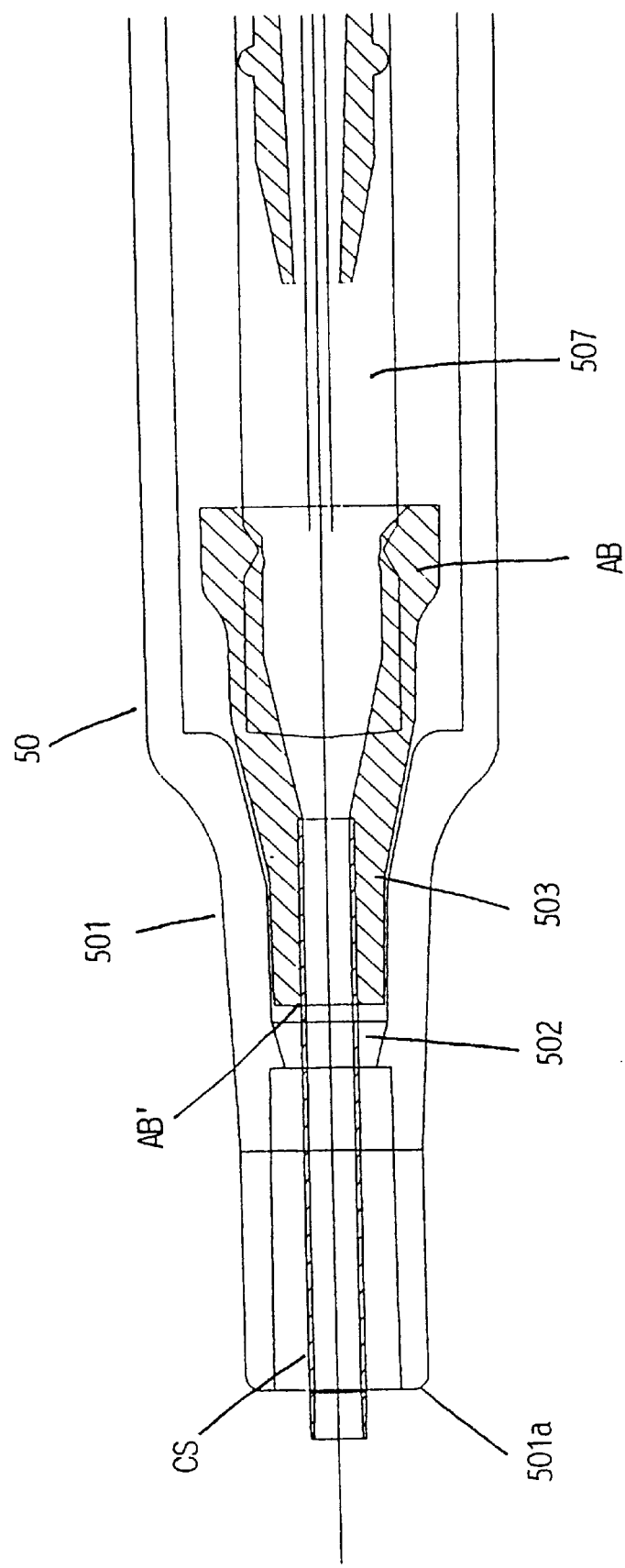
FIG. 22 is a detailed partly sectional view showing the engagement of a shaft accessory with the neck end of the sleeve.

As shown in FIGS. 5 to 8, the sleeve portion 50 has a neck end 501 connectable with the proximal end 3' of the coiled dispenser 3. The neck 501 is shaped to fit over or to be formed integrally with the proximal end 3' and includes an internally formed annular flange 502 which acts as a stop to limit the degree of overlap between the neck and the proximal end 3'. Rearwardly of the flange 502, the interior wall 503 tapers outwardly and is so shaped as to receive the anti-backbleed device AB as a snug fit (FIG. 22). The wall 503 tapers to a shoulder 507, which acts as a stop for the retainer 51.

The main body 504 of the sleeve is circular in cross sectional shape and includes a slot 505 for receiving the retainer 51 in the fashion to be described below. Toward its rearward, open end, the slot 505 includes a pair of cut-outs 506 for receiving complementary noggins of the retainer 51. Sleeve 50 may be fabricated from a suitable plastics or other material.

Figure 8:
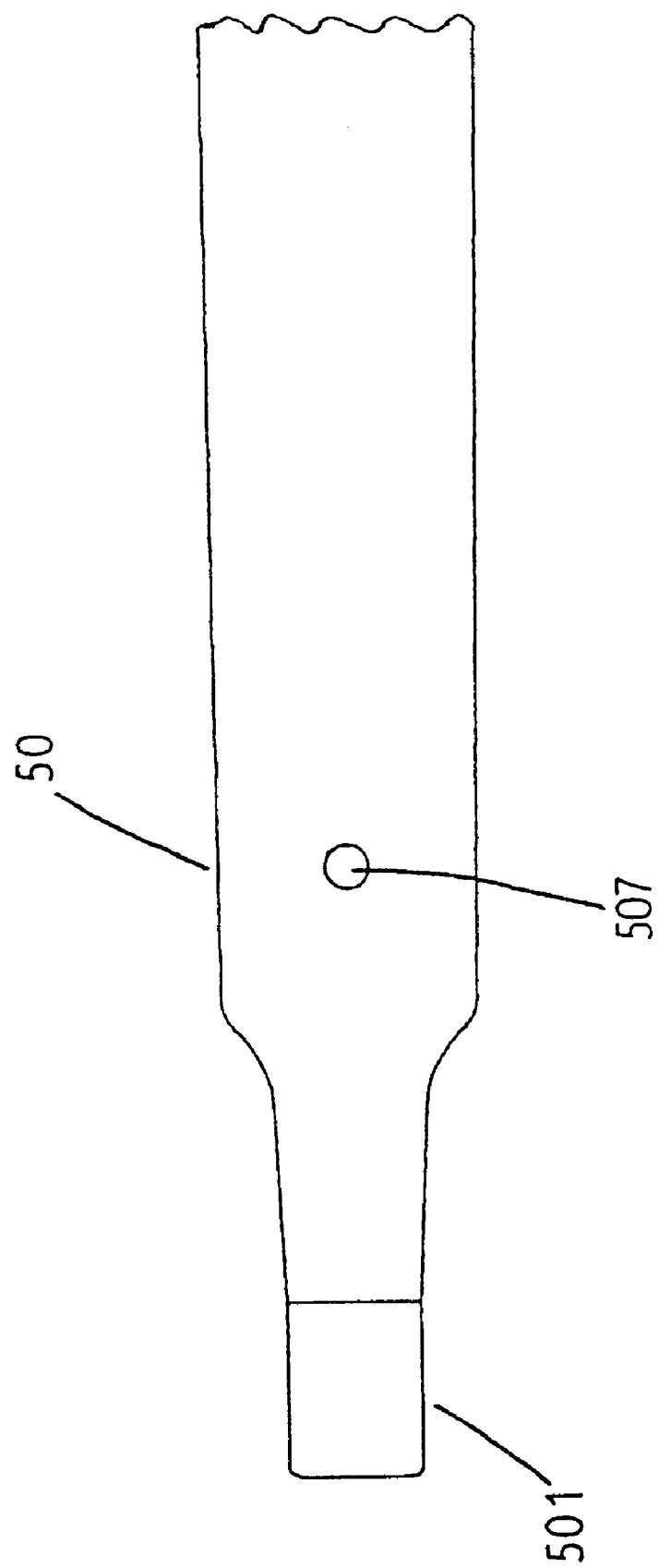
FIG. 8 is a side view of the sleeve.
Figure 16:
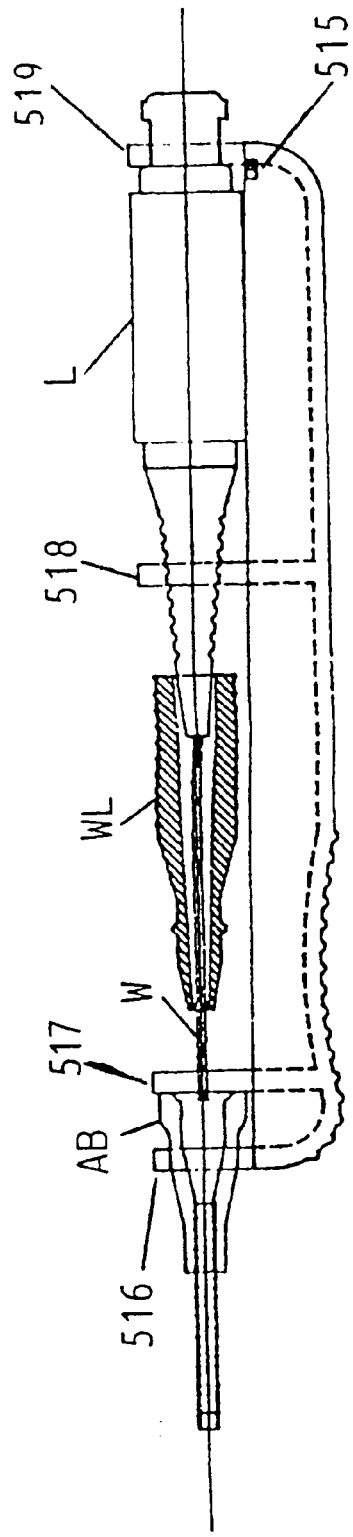
FIG. 16 is a view similar to FIG. 9, with the proximal end of a catheter, together with its fitting, held in the retainer.

In cases where the sleeve 50 is fabricated from an opaque or translucent material, then a viewing port 507 is provided in the main body 504, as shown in FIG. 8. The purpose of the port 507 is described below, with reference to FIG. 22. The port 507 may be formed by cutting away a portion of the main body wall, or it may comprise an inset of a transparent material in the opaque or translucent main body wall. If the main body 504 is fabricated from a transparent material, then the desirability of providing a separate viewing port does not arise.

Turning now to FIGS. 9 to 16, the retainer 51 comprises a skirt 511 on which are mounted a number of catheter wire and accessory gripping elements 516–519. As can be seen in FIG. 11, the skirt 511 is U-shaped in cross section. On the exterior of the base thereof is formed a generally thumb-sized depression 512 which serves as a grip to assist in sliding the retainer 51 out of the sleeve 50. Additionally, the depression 512 is provided with raised ridges 513 to enhance the user's grip. Also embossed on the surface of the underside of the skirt 511 are arrows 514 which guide the user as to the direction in which force should be exerted to withdraw the retainer 51 from the sleeve 50. At the rear of the flange 511 are located a pair of noggins 515, one located on the upper side of each outer-facing arm of the U-shaped skirt, for engaging in the cut-outs 506 of the sleeve 50 to locate the sleeve 50 and retainer 51 together.

Upstanding from the skirt 511 are a number of gripping elements, element 516 being located at the front end of the skirt, element 519 being located at the rear end and elements 517 and 518 being located intermediate the ends. As more clearly seen in FIGS. 12 to 15, each of the elements 516, 518, 519 comprise a pair of opposed curved resilient arms biased toward one another, but sufficiently outwardly flexible to enable them move apart to receive a catheter shaft accessory introduced between the gap between the free ends of the arms. Once a shaft accessory is pressed down between the arms and clears the gap between the free ends of the arms, the arms resume their resting state, so as to hold the accessory in place. In use, element 516 retains an anti-backbleed device AB, element 518 retains a wire lock device WL and element 519 retains a luer fitting L.

FIG. 13 shows more clearly the gripping element 517 which in use retains the catheter wire W. As with elements 516, 518 and 519, element 517 comprises a pair of resilient arms. However, in the case of element 517, the arms define between them a substantially V-shaped gap, in the base of which a catheter wire W is held in use.

A more clear understanding of how the catheter shaft -and accessories are retained by the retainer 51 will be obtained by reference to FIGS. 16 and 18 to 21, which show the anti-backbleed device AB, wire W, wire lock device WL and luer fitting L retained by the elements 516, 517, 518 and 519 respectively.

Figure 17:
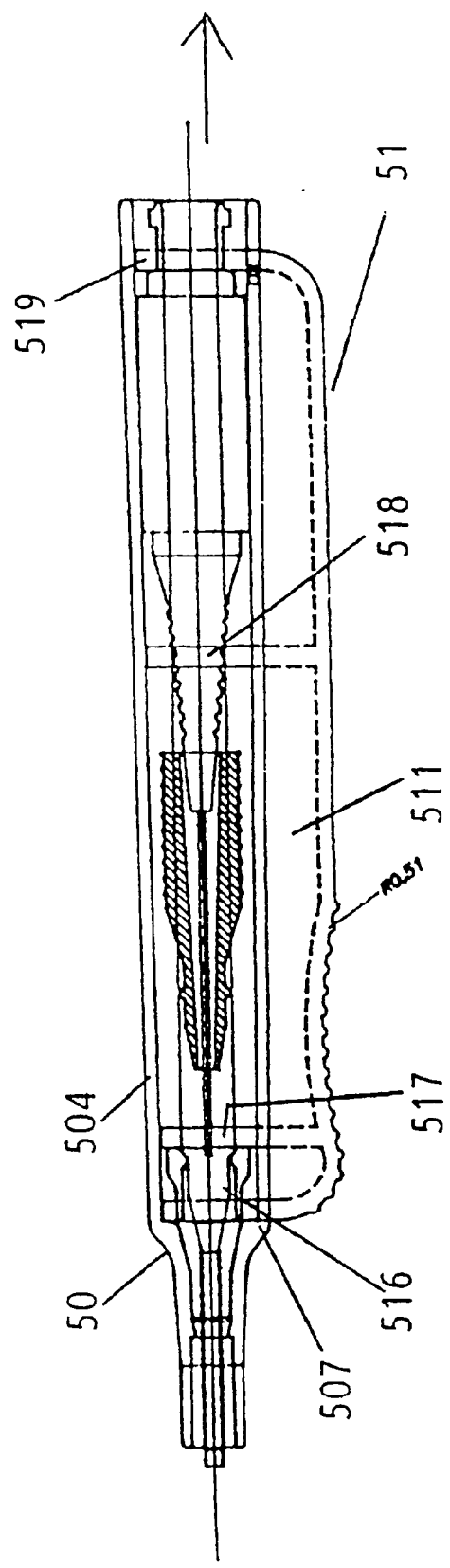
FIG. 17 is a view similar to FIG. 16 with the retainer assembled with a sleeve.
Figure 21:
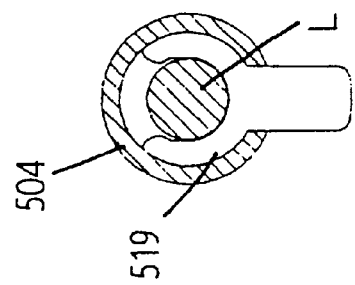
FIGS. 18 to 21 are sectional views taken along the lines B—B, C—C, D—D and E—E respectively of FIG. 17.
Figure 20:
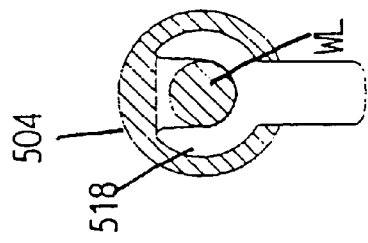
Figure 19:
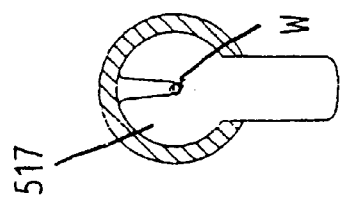
Figure 18:
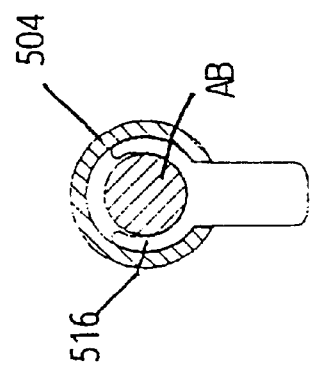

FIG. 17 shows the engagement of the retainer 51 in the sleeve 50. The sleeve 50 is oriented with the slot 505 facing downwardly. The catheter and shaft accessories are retained by the appropriate gripping elements, as described above and the retainer 50 is assembled with the sleeve 51 by holding the skirt 511 and sliding it into and along the slot 505 so that the gripping elements, in the order 516, 517, 518 and finally 519 enter into the interior of the main body 504 of the sleeve 50, guided by the travel of the skirt 511 in the slot 505. The extent of travel of the retainer 51 is limited by the abutment of gripping element 516 with the shoulder 507 and by the closed end of the slot 505 coming into abutment with the front end of the skirt 511. Correct location of the sleeve 50 with the retainer 51 is further assisted by the engagement of the noggins 515 of the skirt 511 with the cut-outs 506 of the sleeve.

For transport and storage, the sleeve 50 is connected to the proximal end 3' of the coiled dispenser 3, the catheter and shaft accessories are pressed into engagement with the respective gripping elements of the retainer 51 and the sleeve 50 and retainer 51 are assembled together as described above. Separation of the retainer 51 from the sleeve 50 is resisted by the engagement of the noggins 515 with the cut-outs 506.

When it is desired to use the catheter, the retainer 51 is slid by the physician out of the sleeve 50 in the direction of the arrow in FIG. 17, with the edges of the slot 505 acting as a guide to ensure that the retainer 51 and assembled catheter parts move axially out of the sleeve 50 and are prevented from rotating relative to the longitudinal axis of the dispenser 3. The physician is assisted in withdrawing the retainer 51 from the sleeve 50 by placing a thumb-pad (or pad of another finger) in the ridged indentation 512 of the skirt 511 and applying an axial force. To ensure that no twisting of the catheter occurs as the retainer 51 is withdrawn, the sleeve 50 is most preferably securely fixed to, or integrally formed with the proximal end 3' of the coiled dispenser 3. In this way, any tendency to rotate the retainer relative to the longitudinal axis of the coiled dispenser will be resisted by the abutment between the walls of the skirt 511 and the wall defining the slot 505. As the catheter wire and shaft accessories are retained positively by the gripping elements, no displacements of the accessories relative to one another or to the shaft are enabled to occur and so the various parts are presented to the physician in the correct order and orientation for use. In this regard, it will be noted that the gripping elements 516, 517, 518 and 519 are sufficiently spaced apart from one another that the various shaft accessories may not become interengaged during storage, transport or use until such time as the physician is ready to operate the various parts. Furthermore, as each accessory is positively retained by the retainer 51, all the accessories are withdrawn from the sleeve 50 at the same time so that the physician wastes no time in attempts to recover from the sleeve any shaft accessory which did not emerge with the luer fitting.

The use of the tri-lock luer 9 (FIGS. 3 and 4) will now be described with particular reference to FIG. 22, which is a detailed view of the neck 501 of the sleeve 50 showing the anti-backbleed device AB engaged in the neck. The interior wall 503 is shaped to receive the anti-backbleed device as a snug fit. Flange 502 acts as a seat or stop for the leading edge AB' of the anti-backbleed device. The catheter shaft or lumen CS (only a short portion of which is shown), extends through the anti-backbleed device, past the flange 502, and on, through the opening 501a of the neck 501, into the coiled dispenser 3. The inside diameter of the flange 502 is matched to the outside diameter of the catheter shaft CS so that a fluid seal is formed between them, but the fit is arranged to be sufficiently free as to enable the catheter shaft to pass the flange 502 without difficulty. The arrangement of the parts is further designed so that when the sleeve 50 is coupled to the coiled dispenser 3, no leakage of fluid can occur at the interface of these parts.

In the manufacture of a PTCA catheter, great care is taken to ensure that no particulate material is trapped in the catheter shaft, as introduction of any such particulate into a patient's body may have very serious consequences. As a further precaution, a catheter is usually prepared for use in a clinic by flushing the interiors of the coiled dispenser and catheter shaft with liquid to dislodge any particulates from the interior of the catheter shaft. In order to do so, the package of the invention includes the tri-lock luer 9 which is connected to the distal end 3" of the coiled dispenser 3. Through an inlet of the tri-lock luer 9, a flushing liquid is introduced into the interior of the dispenser 3. This liquid fills the interior of the coiled dispenser, but is prevented from emerging from the proximal end 3' of the dispenser by reason of the seal formed between the outside surface of the shaft CS and the flange 502 of the neck 501. Liquid also flows into the distal end of the catheter shaft, travels up through the shaft interior, through an anti-backbleed device AB, and emerges from the anti-back bleed device in the region of the viewing port 507 of the sleeve 50. As fluid which enters the cavity of the coiled dispenser is prevented from entering the sleeve 50, the physician can be confident that the lumen of the catheter is unblocked and has been flushed free of particulates by viewing the flow of flushing liquid through the viewing port 507. In the event that no liquid flow is observed, then the physician is alerted to the fact that the catheter lumen is obstructed and can, without significant loss of time, discard the catheter and prepare a fresh one.

While the invention has been described particularly with reference to the form of PTCA catheter commonly referred to as the "over the wire" type, it will be appreciated that with appropriate modifications, it may readily be adapted for PTCA "rapid exchange" type catheters.

It will of course be understood that the invention is not limited to the specific details described herein, which are given by way of example only, and that various modifications and alterations are possible within the scope of the invention as defined in the appended claims.

We claim:

1. A catheter packaging system, comprising:
   a catheter having a proximal end and a distal end including, a catheter shaft having a proximal end and a distal end, and at least one catheter shaft accessory coupled to the proximal end of the catheter shaft;

an elongate tube for receiving the catheter shaft, said elongate tube having a proximal end, a distal end and a longitudinal axis;

a sleeve element extending from the proximal end of the tube having a longitudinal axis coincident with the longitudinal axis of the tube, wherein the sleeve element is sized to accommodate said at least one catheter shaft accessory; and a retaining member for releasably retaining the catheter shaft and said at least one catheter shaft accessory, wherein the retaining member is engageable with the sleeve element and is axially slidable relative to the sleeve element between a storage state in which the retaining member, the catheter shaft and said at least one retained catheter shaft accessory are located substantially within the sleeve element and a usable state in which the retaining member, the catheter shaft and said at least one retained catheter shaft accessory are withdrawn from the sleeve element.

2. A package as claimed in claim 1, wherein guide means are provided to guide the retaining member to be removable from the sleeve element along an axis which is co-axial with the longitudinal axes of the sleeve element and the tube.

3. A package as claimed in claim 2, wherein the guide means comprises a longitudinal slot formed on the sleeve element.

4. A package as claimed in claim 3, wherein the retaining member comprises a key which is engageable with the slot, of the sleeve element.

5. A package as claimed in claim 2, wherein the guide means comprises a slot and the retaining member includes a key sized substantially to match the length and width dimensions of the slot.

6. A package as claimed in claim 5, wherein a portion of the key preferably extends axially outwardly of the slot and that portion is shaped to be gripped by a user to facilitate removal of the retainer member from the sleeve element.

7. A package as claimed in claim 6, wherein the axially outwardly extending portion of the key includes a ridged depression sized to receive a user's finger-pad to assist the user in sliding the retaining means relative to the sleeve element.

8. A package as claimed in any one of claims 1–7, wherein the retaining member further comprises at least one gripping means for releasably retaining at least one of said catheter shaft and said catheter shaft accessory.

9. A package as claimed in claim 8, wherein the gripping means comprises a deformable flexible member sized and arranged to receive at least one of said catheter shaft and said catheter shaft accessory as a snap fit.

10. A package as claimed in any one of claims 1–7 in which flushing means are provided at the distal end of the tube for enabling the interiors of the tube and the catheter contained within the tube to be flushed with flushing fluid from their respective distal to proximal ends.

11. A package as claimed in claim 10 wherein the sleeve element includes a neck portion which is sized and shaped to form a seal between the interior of the proximal end of the tube and the exterior of the proximal end of the catheter shaft, so that flushing fluid is prevented from emerging from the proximal end of the tube thereby ensuring that flushing fluid which issues in the region of the proximal ends has flowed through the interior of the catheter shaft.

12. A package as claimed in claim 11 wherein the sleeve element includes a viewing port adjacent the terminus of the proximal end of the catheter shaft for enabling the user to view the flushing fluid emerging from the terminus.

13. A package as claimed in one of claims 1–7 in which the sleeve element is formed integrally with the tube.

* * * * *